United States Patent
Zhou et al.

(10) Patent No.: US 10,997,720 B2
(45) Date of Patent: May 4, 2021

(54) MEDICAL IMAGE CLASSIFICATION METHOD AND RELATED DEVICE

(71) Applicant: Ping An Technology (Shenzhen) Co., Ltd., Shenzhen (CN)

(72) Inventors: Bo Zhou, New Haven, CT (US); Adam Patrick Harrison, Silver Spring, MD (US); Jiawen Yao, College Park, MD (US); Le Lu, Poolesville, MD (US)

(73) Assignee: Ping An Technology (Shenzhen) Co., Ltd., Shenzhen (CN)

( * ) Notice: Subject to any disclaimer, the term of this patent is extended or adjusted under 35 U.S.C. 154(b) by 99 days.

(21) Appl. No.: 16/546,627

(22) Filed: Aug. 21, 2019

(65) Prior Publication Data

US 2021/0056684 A1    Feb. 25, 2021

(51) Int. Cl.
| | | |
|---|---|---|
| G06T 7/00 | (2017.01) | |
| G16H 30/40 | (2018.01) | |
| G16H 30/20 | (2018.01) | |
| G16H 10/60 | (2018.01) | |
| G06K 9/62 | (2006.01) | |
| G06T 7/11 | (2017.01) | |
| G16H 50/20 | (2018.01) | |

(52) U.S. Cl.
CPC ........... *G06T 7/0012* (2013.01); *G16H 30/20* (2018.01); *G16H 30/40* (2018.01); *G06K 9/6256* (2013.01); *G06K 2209/05* (2013.01); *G06T 7/11* (2017.01); *G16H 10/60* (2018.01); *G16H 50/20* (2018.01)

(58) Field of Classification Search
CPC ......... G06T 7/0012; G06T 7/11; G16H 30/40; G16H 30/20; G16H 50/20; G16H 10/60; G06K 2209/05; G06K 9/6256
USPC ......................................................... 382/128
See application file for complete search history.

(56) References Cited

U.S. PATENT DOCUMENTS

| | | | |
|---|---|---|---|
| 2018/0101768 A1* | 4/2018 | Laine .................. | G06N 3/0472 |
| 2018/0350066 A1* | 12/2018 | Zuyev .................... | G06T 11/60 |
| 2019/0087677 A1* | 3/2019 | Wolf .................... | G06K 9/6271 |
| 2019/0385019 A1* | 12/2019 | Bazrafkan ............. | G06N 3/088 |
| 2020/0151519 A1* | 5/2020 | Anushiravani ......... | G06N 3/08 |

* cited by examiner

*Primary Examiner* — Jerome Grant, II
(74) *Attorney, Agent, or Firm* — ScienBiziP, P.C.

(57) ABSTRACT

A medical image classification method such as CT (or CAT) scans includes receiving the CT scan or medical image, inputting the medical image into an image classification model, which provides a cross entropy (CE) loss function and an aggregated cross entropy (ACE) loss function. According to the ACE loss function, image samples with generic label are used as input data during model training. The medical image can be classified by using the image classification model, and a classification of the medical image is thereby obtained. The present disclosure can classify indeterminate or general medical images and even unlabeled images and thus realize supervision of medical data. A device for applying the method is also provided.

16 Claims, 4 Drawing Sheets

MEDICAL IMAGE CLASSIFICATION METHOD AND RELATED DEVICE

FIELD

Embodiments of the present disclosure relates to classification of images for medical purposes.

BACKGROUND

Electronic or other images of body parts of a patient representing medical conditions can be generated by doctors at the time of diagnosis. Generally, the doctor labels the image to identify which classification the medical image belongs to. However, due to differences in medical experience or habits, different doctors may have differences in labeling medical images. Some labels of medical images may be wrong, some may be unlabeled, and some of medical images may carry a vague and unhelpful explanation. Such medical practices may result in difficulties for a follow-up doctor to use these medical images for treatment.

Therefore, an improved medical image classification method is desired.

DETAILED DESCRIPTION

The present disclosure will be described with reference to the accompanying drawings and specific embodiments. It should be noted that the embodiments of the present disclosure and the non-conflicting features in the embodiments may be combined with each other.

All other embodiments obtained by those skilled in the art based on the embodiments of the present disclosure without creative efforts are within the scope of the present disclosure.

All technical and scientific terms used herein have the same meaning as commonly understood by one of ordinary skill in the art to which this disclosure belongs, unless otherwise defined. The terminology used in the description of the present disclosure is for the purpose of describing particular embodiments and is not intended to limit the disclosure.

The electronic device of the disclosure can automatically perform numerical calculation and/or information processing according to an instruction preset or stored in advance. Hardware of the electronic device may include, but is not limited to, a microprocessor, an application specific integrated circuit (ASIC), programmable gate Arrays (FPGAs), digital signal processors (DSPs), embedded devices, for example. The electronic device may also include a network device and/or a user device.

All of the processes described below may be embodied in, and fully automated via, functional code units executed by one or more general purpose electronic devices or processors. The code units may be stored in any type of non-transitory computer-readable medium or other storage device. Some or all of the methods may alternatively be embodied in specialized hardware. Depending on the embodiment, the non-transitory computer-readable medium may be a hard disk drive, a compact disc, a digital video disc, a tape drive, or other suitable storage medium.

Figure 1:
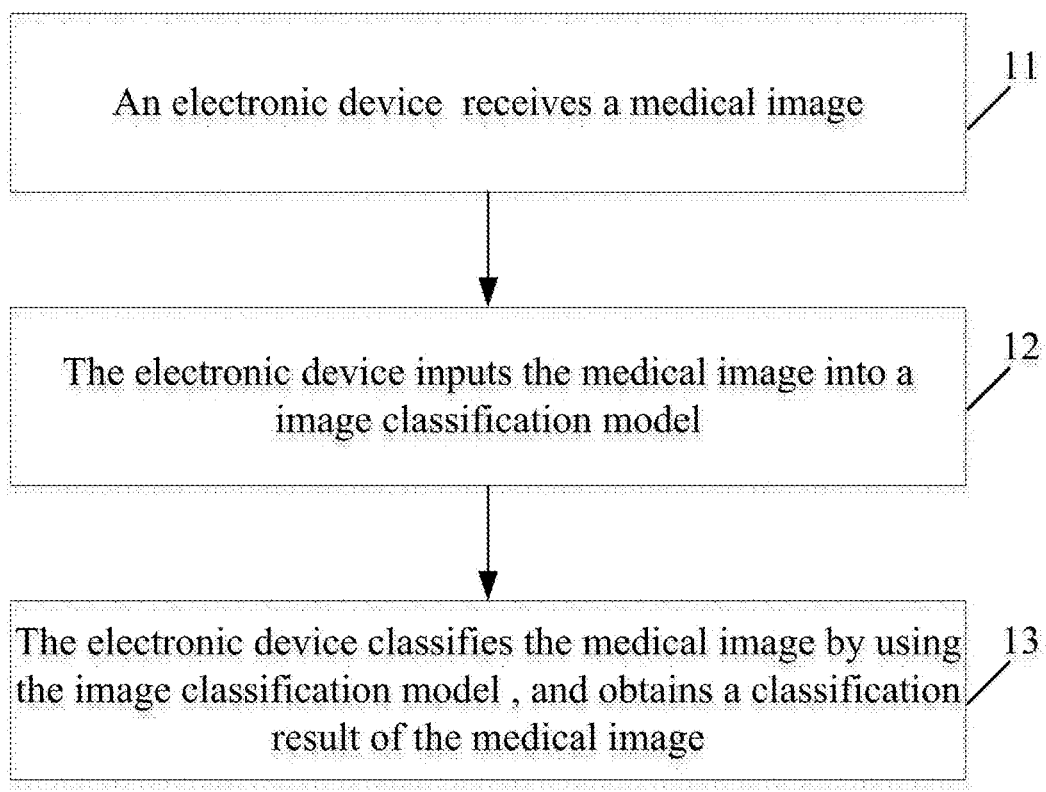
FIG. 1 is a flowchart of one embodiment of a medical image classification method.

FIG. 1 is a flowchart of one embodiment of a medical image classification method. Depending on the embodiment, additional operations may be added, others removed, and the ordering of the blocks may be changed.

In block 11, the electronic device receives a medical image.

In one embodiment, the medical image is an image that needs to be classified, for example, the medical image is a computed tomography (CT) image, and a phase of the CT image needs to be classified. Another example is a magnetic resonance imaging (MRI) scan or Ultrasonography or Elastography scan.

Taking the medical image as a CT image as an example, the CT image can be obtained from Picture Archiving and Communication Systems (PACSs), and the CT image can also be obtained from other systems.

In one embodiment, phases of the CT image may include non-contrast phase, arterial phase, venous phase, and delay phase. The non-contrast phase is when no contrast agent is injected into a body of the person. The non-contrast phase can detect calcifications, fat in tumors, fat-stranding as seen in inflammation like appendicitis, diverticulitis, omental infarction, etc. The arterial phase is when a contrast agent is moved from the left atrium of the heart into the arteries, all structures/organs that get their blood supply from the arteries will show optimal enhancement. In the aorta, a major enhancement can be observed. The venous phase is when the contrast agent flows back from the veins to the heart. In the venous phase, the liver parenchyma enhances through blood supply by the portal vein and some enhancement of the hepatic veins can be seen. The delay phase is when the contrast agent flows out of the kidney. Sometimes delay phase is called "washout phase" or "equilibrium phase". There is wash out of contrast in all abdominal structures except for fibrotic tissue, because fibrotic tissue has a poor late washout and will become relatively dense compared to normal tissue.

Figure 2:
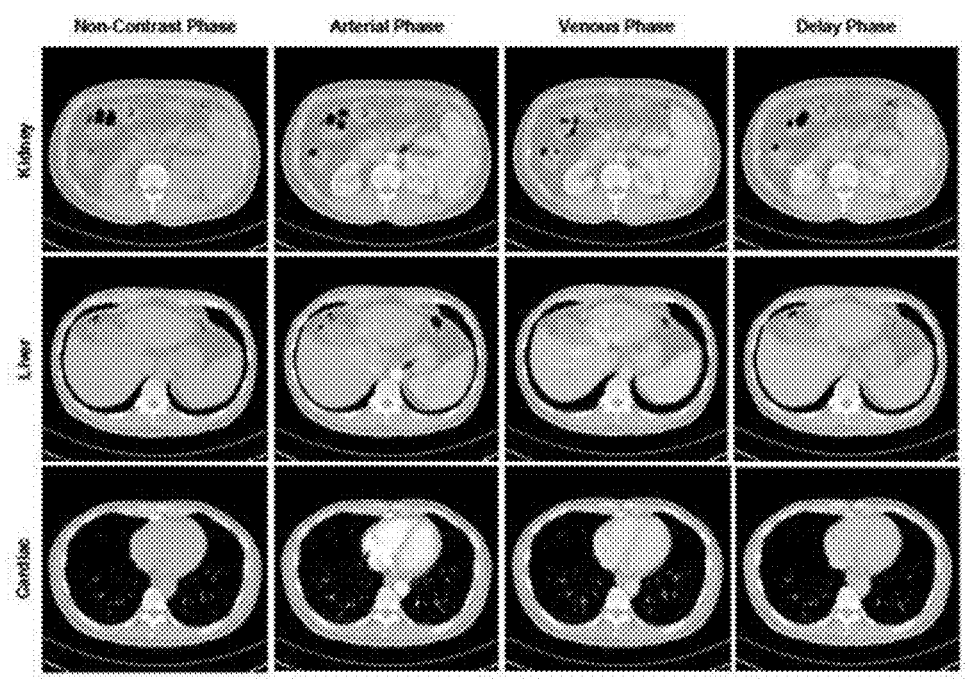
FIG. 2 is a diagram of different phases of a medical image.

FIG. 2 is a diagram of different phases of a medical image. FIG. 2 shows different phases, one in each of the medical images. As shown in FIG. 2, there are four phases, non-contrast agent phase, arterial phase, veins or venous phase, and delay phase. FIG. 2 shows images of three different tissue organs (e.g., kidney, liver, heart) after CT scanning. First row shows CT images of different phases about the kidney, second row shows CT images of different phases about the liver. Third row shows CT images of different phases about the heart. As can be seen from the FIG. 2, CT images of different phases of different organs show changes of light and dark.

In one embodiment, when the CT images are stored in the PACSs, due to differences in medical experience or habits, different doctors may label medical images differently. Some labels of medical images may be wrong, some of medical images may carry no label, and it is difficult to identify phase of the medical images. In another embodiment, the CT images use the Digital Imaging and Communications in Medicine (DICOM) labels. The texts of the DICOM labels only indicate the use of a contrast agent, the CT images that indicate the use of contrast agent may be applied to multiple phases. Thus the actual phase of each of the CT images cannot be distinguished. Accordingly, it is necessary to correctly identify the phase of each of the CT images, and effectively manage the CT images, thus a doctor can directly use the CT image without re-performing CT scanning.

In block 12, the electronic device inputs the medical image into an image classification model.

In one embodiment, the image classification model (e.g., a three dimensional squeeze and excitation (3DSE model) includes a plurality of three dimensional (3D) convolution layers, a squeeze and excitation layer (SE), and a plurality of fully connected layers. For example, the image classification model may include two 3D convolution layers, one SE layer, and two fully connected layers.

In one embodiment, the image classification model provides a cross entropy (CE) loss function and an aggregated cross entropy (ACE) loss function. According to the CE loss function, image samples which have been labeled as one type correctly are used as input data during model training, according to the ACE loss function, image samples with generic (i.e. non-specific) label are used as input data during model training.

In one embodiment, before receiving the medical image, the method further includes:

Obtaining a plurality of medical image samples, the medical image samples including medical image samples labeled as one type, medical image samples with generic label, and unlabeled medical image samples;

Re-sampling the plurality of medical image samples, and obtaining preprocessed image samples with a uniform format;

Extracting partial image features from the preprocessed image samples using a plurality of 3D convolution layers in an initial model framework;

Performing a global pooling operation on the partial image features using an SE layer in the initial model framework, and obtaining a multiplicative factor of each feature channel, and obtaining global image features by weighting the multiplicative factor into the partial image features;

Integrating the global image features by using a plurality of fully connected layers in the initial model framework, and obtaining classification prediction values;

Inputting the classification prediction values into the CE loss function and the ACE loss function, and obtaining a loss value;

Updating parameters of the initial model framework according to the loss value by using a back propagation algorithm;

When the loss value of the CE loss function and the loss value of the ACE loss function are in a convergence state, determining the initial model framework as a trained image classification model after updating the parameters.

In this embodiment, a plurality of medical image samples can be directly obtained from PACSs. The plurality of medical image samples includes medical image samples labeled as one type, medical image samples with generic label, and unlabeled medical image samples. Medical image samples with generic label indicate the use of contrast agent may be applied to multiple phases. The plurality of medical image samples include all possible cases. Due to the medical image samples being of different sizes, each medical image sample needs to be resampled and preprocessed image samples with a uniform format are then obtained. For example, the medical image samples can be unified into a 128×128×32 image sample.

The preprocessed image samples are input into an initial model framework. Parameters in the initial model framework need to be determined after the model training, and the initial model framework includes two 3D convolution layer (3×3×3), one SE, and two fully connected layers. Moreover, two 3D convolution layers in the initial model framework are used to perform convolution operation for the preprocessed image samples. Partial image features are extracted from the preprocessed image samples by performing a linear rectification function and a maximum pooling operation (1×2×2). The partial image features indicate that the extracted feature is partial, it further needs to add global information into each feature channel through the SE layer. Moreover, the partial image features can be globally pooled using the SE layer in the initial model framework, and a multiplicative factor of each feature channel is obtained, the multiplicative factor being weighted into the partial image feature to scale each feature channel. A global image feature is thereby obtained. In one embodiment, after a maximum pooling operation (2×2×2), the average pooling operation (16×16), and flattening, a process of the global image feature is obtained. The process of the global image feature is input into a plurality of fully connected layers in the initial model framework for integration, and a classification prediction value is obtained.

Finally, the classification prediction value is input into the CE loss function and the ACE loss function, and a loss value is obtained. Parameters (e.g., convolutional kernel parameter, and weights parameter) of the initial model framework are updated according to the loss value by using a back propagation algorithm. When the loss value of the CE loss function is in a convergence state, and the loss value of the ACE loss function is in a convergence state, the initial model framework is determined as a trained image classification model after the updating of the parameters.

Operations of the SE layer may referred to related art, and details are not described herein again.

In one embodiment, taking the medical image as a CT image as an example, the classification prediction value may be seen as a phase prediction value. The phase prediction value includes non-contrast phase prediction value, arterial phase prediction value, venous phase prediction value, delay phase prediction value, and no phase prediction value.

Specifically, the inputting of the classification prediction values into the CE loss function and the ACE loss function, and the obtaining of a loss value includes:

Inputting the classification prediction values corresponding to medical image samples labeled as one type into the CE loss function, and obtaining a loss value of the CE loss function;

Inputting the classification prediction values corresponding to medical image samples with generic label into the ACE loss function, and obtaining a loss value of the ACE loss function.

During model training, after medical image samples labeled as one type are trained, classification prediction values obtained are also labeled as one type. After medical image samples with generic label is trained, classification prediction values obtained are also with generic label, thus according to the requirements of different loss functions, the classification prediction values corresponding to medical image samples labeled as one type are input into the CE loss function, and a loss value of the CE loss function is obtained. The classification prediction values corresponding to medical image samples with generic label are also input into the ACE loss function, and a loss value of the ACE loss function is obtained. The CE loss function and the ACE loss function are used to simultaneously calculate the classification prediction value output by the initial model framework, and whether the initial model framework is detected as a correct train or as an incorrect training according to the convergence of the loss value.

In another embodiment, the method further includes:

Calculating a probability of a different classification of the medical image samples by using a normalized exponential function;

Constructing a classification probability relationship according to the calculated probability;

Constructing the ACE loss function according to the classification probability relationship and the CE loss function.

In one embodiment, the classification probability relationship can be expressed as:

$$PC = PA + PV + PD = \frac{\exp(WA) + \exp(WV) + \exp(WD)}{\Sigma_i \exp(wi)}$$

The PC is a total probability of a phase prediction value of the arterial, of the venous, and of the delay phase. The PA is a probability of a phase prediction value of the arterial phase, the PV is a probability of a phase prediction value of the venous phase, and the PD is a probability of a phase prediction value of delay phase. Exp( . . . ) is an exponential function, w( . . . ) is a logarithmic function, and i is a positive integer. Further, The ACE loss function is expressed as:

$$L_{ACE} = -\log(PC) = -\log\left(\frac{\exp(WA) + \exp(WV) + \exp(WD)}{\Sigma_i \exp(wi)}\right)$$

where log( . . . ) is a logarithmic function.

In this embodiment, the normalized exponential function, for example the Softmax function, can be used to calculate the probability of different classifications of the medical image samples, such as PC, PA, PV, PD, for example. Since the PC includes three, it is possible to construct a classification probability relation and construct the ACE loss function based on the CE loss function.

The CE loss function can be expressed as:

$$L_{CE} = -y_{NC} \log(P_{NC}) - y_O \log(P_O) - y_C \log(P_C)$$

where $y_{NC}$ represents a value of a real sample label of non-contrast phase, $P_{NC}$ is a probability of a phase prediction value of non-contrast phase, and $y_O$ represents a value of a real sample label that does not represent any phase. $P_O$ is a probability of a phase prediction value of a label that does not represent any phase, $y_C$ represents a value of a real sample label of arterial phase and venous phase and delay phase, and $P_C$ is a probability of phase prediction values of each of the three phases.

The above ACE loss function can be obtained by configuring $y_{NC}=0$, $y_O=0$, $y_C=1$.

By comparison with the previous residual network 3D-Resnet, the spatio-temporal feature network C3D, the image classification model trained according to the above method has a small number of parameters, and low memory is needed.

The image classification model with or without the ACE loss function can be tested on a data set, and the image classification model is compared with a text mining model, the 3D-Resnet model, and the C3D model. The image classification model of the ACE loss function can utilize the data as much as possible, and an F1 score of the image classification model based on the ACE loss function is significantly higher than that of the image classification model, which is not based on the ACE loss function and other models (e.g., the text mining model, the 3D-Resnet model, and the C3D model). The F1 score is used to measure an accuracy of image classification for models.

In block 13, the electronic device classifies the medical image by using the image classification model, and obtains a classification of the medical image.

For example, when the medical image is a CT image, the electronic device classifies the medical image by using the image classification model, and obtains a classification in the following way:

The electronic device classifies the CT image by using the image classification model, and obtains a classification of the CT image, the CT image includes images of non-contrast phase or arterial phase or venous phase or delay phase.

Figure 3:
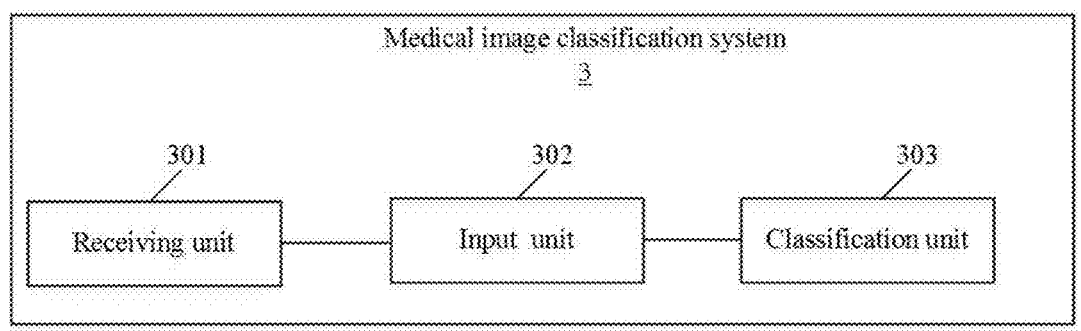
FIG. 3 is a block diagram of one embodiment of a medical image classification system.

FIG. 3 is a block diagram of one embodiment of a medical image classification system.

In some embodiments, the medical image classification system 3 operates in an electronic device. The medical image classification system 3 may include a plurality of functional modules consisting of program code segments. The program code of each of the program segments in the medical image classification system 3 may be stored in a memory and executed by at least one processor to perform some or all of the steps in the medical image classification method described in FIG. 1.

In one embodiment, the medical image classification system 3 may be divided into a plurality of functional modules according to functions performed thereby. The functional modules may include a receiving unit 301, an input unit 302, and a classification unit 303. A module as referred to in the present disclosure refers to a series of computer program segments that can be executed by at least one processor and that are capable of performing fixed functions, which are stored in a memory. In some embodiments, the functionality of each module will be detailed.

The receiving unit 301 is configured to receive a medical image.

In one embodiment, the medical image is an image that needs to be classified, for example, the medical image is a computed tomography (CT) image, and a phase of the CT image needs to be classified. Other examples are that the medical image is magnetic resonance imaging (MRI) scan or Ultrasonography or Elastography scan.

Taking the medical image as a CT image as an example, the CT image can be obtained from Picture Archiving and Communication Systems (PACSs), and the CT image can also be obtained from other systems.

In one embodiment, phases of the CT image may include non-contrast phase or arterial phase or venous phase or delay phase. The non-contrast phase is used to label that no contrast agent is injected into a body of the person. In the non-contrast phase, it is helpful in detecting calcifications, fat in tumors, fat-stranding as seen in inflammation like appendicitis, diverticulitis, omental infarction, etc. The arterial phase is used to label that contrast agent is ejected from the left atrium of the heart into the artery, all structures/organs that get their blood supply from the arteries will show optimal enhancement. In the aorta, a major enhancement can be observed. The venous phase is used to label contrast agent flowing back from the vein to the heart. In the venous phase, the liver parenchyma enhances through blood supply by the portal vein and some enhancement of the hepatic veins can be seen. The delay phase is used to label that the contrast agent flows out of the kidney. Sometimes delay phase is called "washout phase" or "equilibrium phase". There is wash out of contrast in all abdominal structures except for fibrotic tissue, because fibrotic tissue has a poor late washout and will become relatively dense compared to normal tissue.

FIG. 2 is a diagram of different phases of a medical image. As shown in FIG. 2, there are four phases, non-contrast agent phase, arterial phase, veins or venous phase, and delay phase. FIG. 2 shows images of three different tissue organs (e.g., kidney, liver, heart) after CT scanning. First row shows CT images of different phases about the kidney, second row shows CT images of different phases about the liver. Third row shows CT images of different phases about the heart. As can be seen from the FIG. 2, CT images of different phases of different organs shows changes of light and dark.

In one embodiment, when the CT images are stored in the PACSs, due to differences in medical experience or habits, different doctors may label medical images differently. Some labels of medical images may be wrong, some of medical images may carry no label, and it is difficult to identify phase of the medical images. In another embodiment, the CT images use the Digital Imaging and Communications in Medicine (DICOM) labels. The texts of the DICOM labels only indicate the use of a contrast agent, the CT images that indicate the use of contrast agent may be applied to multiple phases. Thus the actual phase of each of the CT images cannot be distinguished. Accordingly, it is necessary to correctly identify the phase of each of the CT images, and effectively manage the CT images, thus a doctor can directly use the CT image without re-performing CT scanning.

The input unit 302 is configured to input the medical image into an image classification model.

In one embodiment, the image classification model (e.g., a three dimensional squeeze and excitation (3DSE) model) includes a plurality of three dimensional (3D) convolution layers, a squeeze and excitation layer (SE), and a plurality of fully connected layers. For example, the image classification model may include two 3D convolution layers, one SE layer, and two fully connected layers.

In one embodiment, the image classification model provides a CE loss function and an ACE loss function. According to the CE loss function, image samples which have been labeled as one type correctly are used as input data during model training, according to the ACE loss function, image samples with generic (i.e. non-specific) label are used as input data during model training.

In one embodiment, the medical image classification system 3 further includes an obtaining unit, a re-sampling unit, an extracting unit, a performing unit, an integrating unit, an updating unit and a determination unit.

The obtaining unit is configured to obtain a plurality of medical image samples before the receiving unit 301 receives the medical image. The medical image samples include medical image samples labeled as one type, medical image samples with generic label, and unlabeled medical image samples The re-sampling unit is configured to re-sample the plurality of medical image samples, obtaining a preprocessed image samples with a uniform format;

The extracting unit is configured to extract partial image features from the preprocessed image samples using a plurality of 3D convolution layers in an initial model framework;

The performing unit is configured to perform a global pooling operation on the partial image features using a SE layer in the initial model framework, obtaining a multiplicative factor of each feature channel, and obtaining global image features by weighting the multiplicative factor into the partial image features;

The integrating unit is configured to integrate the global image features by using a plurality of fully connected layers in the initial model framework, obtaining classification prediction values;

The input unit 302 is further configured to input the classification prediction values into the CE loss function and the ACE loss function, obtaining a loss value;

The updating unit is configured to update parameters of the initial model framework according to the loss value by using a back propagation algorithm;

The determination unit is configured to determine the initial model framework as a trained image classification model after updating the parameters when the loss value of the CE loss function and the loss value of the ACE loss function are in a convergence state.

In this embodiment, a plurality of medical image samples can be directly obtained from PACSs. The plurality of medical image samples includes medical image samples labeled as one type, medical image samples with generic label, and unlabeled medical image samples. Medical image samples with generic label indicate the use of contrast agent may be applied to multiple phases. The plurality of medical image samples includes all possible cases. Due to the medical image samples having different sizes, the medical image samples need to be resampled, and preprocessed image samples with a uniform format obtained. For example, the plurality of medical image samples are unified into a 128×128×32 image sample.

The preprocessed image samples are input into an initial model framework. Parameters in the initial model framework need to be determined after the model training, and the initial model framework includes two 3D convolution layer (3×3×3), one SE, and two fully connected layers. Moreover, two 3D convolution layers in the initial model framework are used to perform convolution operation for the preprocessed image samples. Partial image features are extracted from the preprocessed image samples by performing a linear rectification function and a maximum pooling operation (1×2×2). The partial image features indicate that the extracted feature is partial, it further needs to add global information into each feature channel through the SE layer. Moreover, the partial image features can be globally pooled using the SE layer in the initial model framework, and a multiplicative factor of each feature channel is obtained, the multiplicative factor being weighted into the partial image feature to scale each feature channel. A global image feature is thereby obtained. In one embodiment, after a maximum pooling operation (2×2×2), the average pooling operation (16×16), and flattening, a process of the global image feature is obtained. The process of the global image feature is input into a plurality of fully connected layers in the initial model framework for integration, and a classification prediction value is obtained.

Finally, the classification prediction value is input into the CE loss function and the ACE loss function, and a loss value is obtained. Parameters (e.g., convolutional kernel parameter, weights parameter) of the initial model framework are updated according to the loss value by using a back propagation algorithm. When the loss value of the CE loss function is in a convergence state, and the loss value of the ACE loss function is in a convergence state, the initial model framework is determined as a trained image classification model after the updating of the parameters.

Operations of the SE layer may referred to related art, and details are not described herein again.

In one embodiment, taking the medical image as a CT image as an example, the classification prediction value may be seen as a phase prediction value. The phase prediction value includes non-contrast phase prediction value, arterial phase prediction value, venous phase prediction value, delay phase prediction value, and no phase prediction value.

Specifically, the input unit 302 is specifically configured to:

Input the classification prediction values corresponding to medical image samples labeled as one type into the CE loss function, obtaining a loss value of the CE loss function;

Input the classification prediction values corresponding to medical image samples with generic label into the ACE loss function, obtaining a loss value of the ACE loss function.

During model training, after medical image samples labeled as one type is trained, classification prediction values obtained are also labeled as one type, after medical image samples with generic label is trained, classification prediction values obtained are also with generic label, thus according to the requirements of different loss functions, the classification prediction values corresponding to medical image samples labeled as one type are input into the CE loss function, and a loss value of the CE loss function is obtained, the classification prediction values corresponding to medical image samples with generic label are input into the ACE loss function, and a loss value of the ACE loss function is obtained. The CE loss function and the ACE loss function are used to simultaneously calculate the classification prediction value output by the initial model framework, and whether the initial model framework is detected as a correct train or as an incorrect training according to the convergence of the loss value.

In another embodiment, the medical image classification system 3 further includes a calculating unit and a constructing unit.

The calculating unit is configured to calculate a probability of a different classification of the medical image samples by using a normalized exponential function;

The constructing unit is configured to construct a classification probability relationship according to the calculated probability;

The constructing unit is configured to construct the ACE loss function according to the classification probability relationship and the CE loss function.

In one embodiment, the classification probability relationship can be expressed as:

$$PC = PA + PV + PD = \frac{\exp(WA) + \exp(WV) + \exp(WD)}{\Sigma_i \exp(wi)}$$

wherein the PC is a total probability of a phase prediction value of the arterial, of the venous, and of the delay phase, the PA is a probability of a phase prediction value of the arterial phase, the PV is a probability of a phase prediction value of the venous phase, the PD is a probability of a phase prediction value of the delay phase, exp( . . . ) is an exponential function, w( . . . ) is a logarithmic function, and i is a positive integer; and The ACE loss function is expressed as:

$$L_{ACE} = -\log(PC) = -\log\left(\frac{\exp(WA) + \exp(WV) + \exp(WD)}{\Sigma_i \exp(wi)}\right)$$

log( . . . ) is a logarithmic function.

In this embodiment, the normalized exponential function, for example the Softmax function, can be used to calculate the probability of different classifications of the medical image samples, such as PC, PA, PV, PD, for example. Due to the situation that the PC includes three, it is possible to construct a classification probability relation and construct the ACE loss function based on the CE loss function.

The CE loss function can be expressed as:

$$L_{CE} = -y_{NC}\log(P_{NC}) - y_O\log(P_O) - y_C\log(P_C)$$

where $y_{NC}$ represents a value of a real sample label of non-contrast phase, $P_{NC}$ is a probability of a phase prediction value of non-contrast phase, and $y_O$ represents a value of a real sample label that does not represent any phase, $P_O$ is a probability of a phase prediction value of a label that does not represent any phase, $y_C$ represents a value of a real sample label of arterial phase and venous phase and delay phase, and $P_C$ is a probability of a phase prediction values of each of the three phases.

The above ACE loss function can be obtained by configuring $y_{NC}=0$, $y_O=0$, $y_C=1$.

By comparison with the previous residual network 3D-Resnet, the spatio-temporal feature network C3D, the image classification model trained according to the above method has a small number of parameters, and low memory is needed.

The image classification model with or without the ACE loss function can be tested on a data set, and the image classification model is compared with a text mining model, the 3D-Resnet model, and the C3D model. The image classification model of the ACE loss function can utilize the data as much as possible, and an F1 score of the image classification model based on the ACE loss function is significantly higher than the image classification model, which is not based on the ACE loss function and other models (e.g., the text mining model, the 3D-Resnet model, and the C3D model). The F1 score is used to measure an accuracy of image classification for model.

The classification unit 303 is configured to classify the medical image by using the image classification model, and obtains a classification result of the medical image.

For example, the medical image is a CT image, the classifying unit 303 is specifically configured to classify the CT image by using the image classification model, and obtains a classification result of the CT image, the CT image includes non-contrast phase or arterial phase or venous phase or delay phase.

Figure 4:
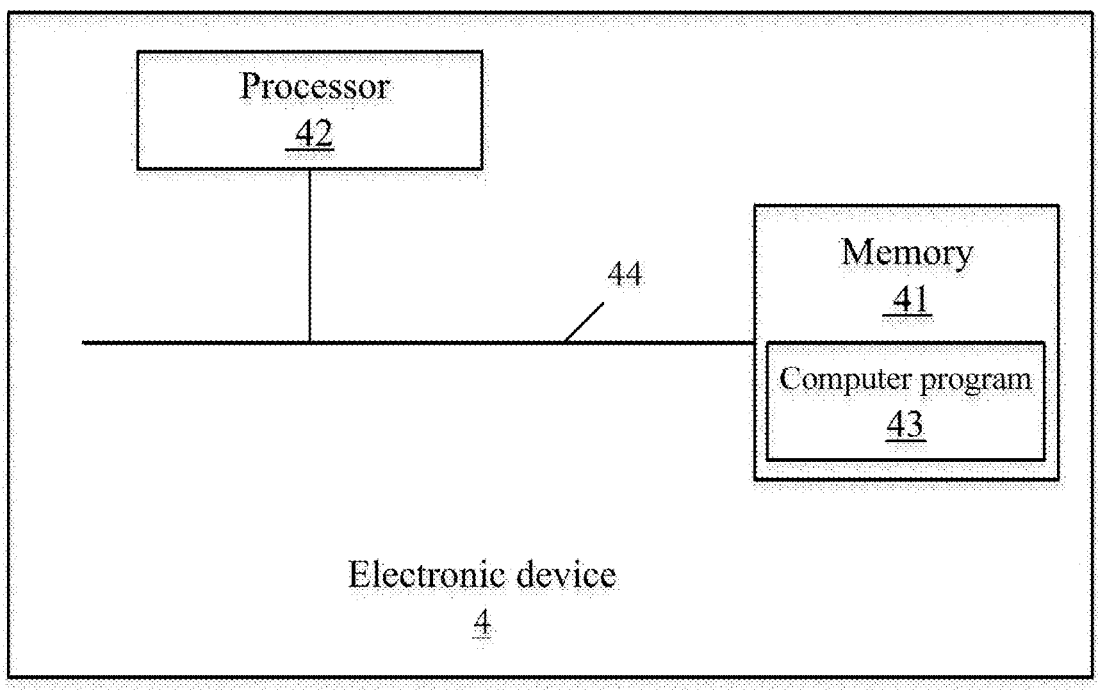
FIG. 4 is a block diagram of one embodiment of an electronic device.

FIG. 4 is a block diagram of one embodiment of an electronic device.

The electronic device 4 includes a memory 41, at least one processor 42, a computer program 43 stored in the memory 41 and operable on the at least one processor 42, and at least one communication bus 44.

It will be understood by those skilled in the art that FIG. 4 is merely showing an example of the electronic device 4, it does not constitute a limitation on the electronic device 4, it may include more or less components than those illustrated, or may combine certain components, or different components. The electronic device 4 may also include input and output devices, network access devices, and the like.

The electronic device includes an electronic device capable of automatically performing numerical calculation and/or information processing according to an instruction set or stored in advance, the hardware of which includes but is not limited to a microprocessor, an application specific integrated circuit (ASIC), a programmable gate Arrays (FP- GAs), digital processors (DSPs), embedded devices, and the like. The electronic device may also include a network device and/or a user device. The network device includes, but is not limited to, a single network server, a server group composed of multiple network servers, or a cloud computing-based cloud composed of a large number of hosts or network servers, where the cloud computing is distributed computing. A super virtual computer consists of a group of loosely coupled computers. The user equipment includes, but is not limited to, any electronic product that can interact with a user through a keyboard, a mouse, a remote controller, a touch pad, or a voice control device, such as a personal computer, a tablet computer, a smart phone, a personal digital device, assistant PDA, game console, interactive network TV IPTV, smart wearable device, and others. The network in which the user equipment and the network device are located includes, but is not limited to, the Internet, a wide area network, a metropolitan area network, a local area network, a virtual private network (VPN), and the like.

The at least one processor 42 may be a central processing unit (CPU), or may be another general-purpose processor, a digital signal processor (DSP), or an application specific integrated circuit (ASIC), a Field-Programmable Gate Array (FPGA) or other programmable logic device, discrete gate or transistor logic device, discrete hardware components, and the like. The processor 42 may be a microprocessor or the processor 42 may be any conventional processor or the like. The processor 42 is a control center of the electronic device 4, and connects various parts of the entire electronic device 4 by using various interfaces and lines.

The memory 41 can be used to store the computer program 43 and/or modules/units by running or executing computer programs and/or modules/units stored in the memory 41, and by calling in memory. The data within memory 41 implements various functions of the electronic device 4. The memory 41 may mainly include a storage program area and a storage data area, wherein the storage program area may store an operating system, an application required for at least one function (such as a sound playing function, an image playing function, etc.), and the like. Data created by the use of the electronic device 4 is also stored. In addition, the memory 41 may include a non-volatile memory such as a hard disk, a memory, a plug-in hard disk, a smart memory card (SMC), and a secure digital (SD) card, flash card, at least one disk storage device, flash device, or other non-volatile solid state storage device.

Combined with FIG. 1, the memory 41 in the electronic device 4 stores a plurality of instructions to implement a medical image classification method, and when the memory 41 is executed by the processor 42, causes the processor 42 to:

receive a medical image;

input the medical image into an image classification model, which provides a cross entropy (CE) loss function and an aggregated cross entropy (ACE) loss function, wherein according to the ACE loss function, image samples with generic label are used as input data during model training;

classify the medical image by using the image classification model, and obtain a classification result of the medical image.

In some implementation, the image classification model includes a plurality of three dimensional (3D) convolution layers, a Squeeze and Excitation (SE) layer, and a plurality of fully connected layers.

In some implementations, before receive the medical image, the processor 42 further:

obtains a plurality of medical image samples, the medical image samples including medical image samples labeled as one type, medical image samples with generic label, and unlabeled medical image samples;

re-samples the plurality of medical image samples, and obtains preprocessed image samples with a uniform format;

extracts partial image features from the preprocessed image samples using a plurality of three dimensional (3D) convolution layers in an initial model framework;

performs a global pooling operation on the partial image features using a Squeeze and Excitation (SE) layer in the initial model framework, and obtains a multiplicative factor of each feature channel, and obtains global image features by weighting the multiplicative factor into the partial image features;

integrates the global image features by using a plurality of fully connected layers in the initial model framework, and obtains classification prediction values;

inputs the classification prediction values into the CE loss function and the ACE loss function, and obtains a loss value;

updates parameters of the initial model framework according to the loss value by using a back propagation algorithm;

when the loss value of the CE loss function and the loss value of the ACE loss function are in a convergence state, determines the initial model framework as a trained image classification model after updating the parameters.

In some implementations, the processor further 42:

inputs the classification prediction values corresponding to medical image samples labeled as one type into the CE loss function, obtaining a loss value of the CE loss function;

inputs the classification prediction values corresponding to medical image samples with generic label into the ACE loss function, obtaining a loss value of the ACE loss function.

In some implementations, the processor 42 further:

calculates a probability of different classification of the medical image samples by using a normalized exponential function;

constructs a classification probability relationship according to the calculated probabilities;

constructs the ACE loss function according to the classification probability relationship and the CE loss function.

In some implementations, wherein the medical image is a computed tomography (CT) image, the processor 42 further:

classifies the CT image by using the image classification model, and obtains a classification of the CT image, the CT image includes non-contrast phase or arterial phase or venous phase or delay phase.

In some implementations, wherein the medical image is a computed tomography (CT) image, the processor 42 further:

classifies the CT image by using the image classification model, and obtains a classification of the CT image, the CT image includes non-contrast phase or arterial phase or venous phase or delay phase.

In some implementations, wherein the medical image is a computed tomography (CT) image, the processor 42 further:

classifies the CT image by using the image classification model, and obtains a classification of the CT image, the CT image includes non-contrast phase or arterial phase or venous phase or delay phase.

In some implementations, wherein the medical image is a computed tomography (CT) image, the processor 42 further:

classifies the CT image by using the image classification model, and obtains a classification of the CT image, the CT image includes non-contrast phase or arterial phase or venous phase or delay phase.

In some implementations, wherein the classification probability relationship is expressed as:

$$PC = PA + PV + PD = \frac{\exp(WA) + \exp(WV) + \exp(WD)}{\Sigma_i \exp(wi)}$$

wherein the PC is a total probability of a phase prediction value of the arterial, of the venous, and of the delay phase, the PA is a probability of a phase prediction value of arterial phase, the PV is a probability of a phase prediction value of venous phase, the PD is a probability of a phase prediction value of delay phase, exp( . . . ) is an exponential function, w( . . . ) is a logarithmic function, and i is a positive integer; and the ACE loss function is expressed as:

$$L_{ACE} = -\log(PC) = -\log\left(\frac{\exp(WA) + \exp(WV) + \exp(WD)}{\Sigma_i \exp(wi)}\right)$$

log( . . . ) is a logarithmic function.

For details, refer to the description of the related steps in the corresponding embodiment of FIG. 1 for the specific implementation of the above-mentioned instructions by the processor 42, and details are not described herein.

In the above mentioned method, the medical image can be classified by using an image classification model based on the CE loss function and the ACE loss function, a classification obtained can be used to distinguish medical image samples with generic label, the classification result is precise. Thereby, medical data can be effectively managed.

The modules/units integrated by the electronic device 4, if implemented in the form of software functional units as separate products, may be stored in a computer readable storage medium. Based on such understanding, the present disclosure implements all or part of the processes in the foregoing embodiments, and may also be completed by a computer program to instruct related hardware. The computer program may be stored in a computer readable storage medium. The steps of the various method embodiments described above may be implemented when the program is executed by the processor. Wherein, the computer program includes computer program code, which may be in the form of source code, object code form, executable file, or some intermediate form. The computer readable medium may include any entity or device capable of carrying the computer program code, a recording medium, a USB flash drive, a removable hard disk, a magnetic disk, an optical disk, a computer memory, a read-only memory (ROM).

In the several embodiments provided by the present disclosure, it should be understood that the disclosed system, apparatus, and method may be implemented in other manners. For example, the device embodiments described above are merely illustrative. For example, the division of the modules is only a logical function division, and the actual implementation may have another manner of division.

The modules described as separate components may or may not be physically separated, and the components displayed as modules may or may not be physical units, that is, may be located in one place, or may be distributed in multiple network units. Some or all of the modules may be selected according to actual needs to achieve the purpose of the solution of the embodiment.

In addition, each functional module in each embodiment of the present disclosure may be integrated into one processing unit, or each unit may exist physically separately, or two or more units may be integrated into one unit. The above integrated unit can be implemented in the form of hardware or in the form of hardware plus software function modules.

It is apparent to those skilled in the art that the present disclosure is not limited to the details of the above-described exemplary embodiments, and the present disclosure can be embodied in other specific forms without departing from the spirit or essential characteristics of the present disclosure. Therefore, the present embodiments are to be considered as illustrative and not restrictive, and the scope of the present disclosure is defined by the appended claims instead all changes in the meaning and scope of equivalent elements are included in the present disclosure. Any accompanying drawings in the claims should not be construed as limiting the claim. In addition, it is to be understood that the word "including" does not exclude other elements or steps. A plurality of units or devices recited in the system claims can also be implemented by a unit or device by software or hardware. The particular ordering of words does not denote any particular order.

It should be noted that the above embodiments are only for explaining the technical solutions of the present disclosure and are not intended to be limiting, and the present disclosure will be described in detail with reference to the preferred embodiments. Modifications or equivalents are made without departing from the spirit and scope of the present disclosure.

What is claimed is:

1. A medical image classification method, comprising:
   receiving a medical image;
   inputting the medical image into an image classification model, which provides a cross entropy (CE) loss function and an aggregated cross entropy (ACE) loss function, wherein according to the ACE loss function, image samples with generic label are used as input data during model training, wherein the image classification model comprises a plurality of three dimensional (3D) convolution layers, a squeeze and excitation (SE) layer and a plurality of fully connected layers;
   classifying the medical image by using the image classification model and obtaining a classification result of the medical image.

2. The medical image classification method of claim 1, before receiving the medical image, further comprising:
   obtaining a plurality of medical image samples, the medical image samples comprising medical image samples labeled as one type, medical image samples with generic label, and unlabeled medical image samples;
   re-sampling the plurality of medical image samples, and obtaining preprocessed image samples with a uniform format;
   extracting partial image features from the preprocessed image samples using a plurality of three dimensional (3D) convolution layers in an initial model framework;
   performing a global pooling operation on the partial image features using a squeeze and excitation (SE) layer in the initial model framework, and obtaining a multiplicative factor of each feature channel, and obtaining global image features by weighting the multiplicative factor into the partial image features;
   integrating the global image features by using a plurality of fully connected layers in the initial model framework, and obtaining classification prediction values;
   inputting the classification prediction values into the CE loss function and the ACE loss function, and obtaining a loss value;

updating parameters of the initial model framework according to the loss value by using a back propagation algorithm;

when the loss value of the CE loss function and the loss value of the ACE loss function are in a convergence state, determining the initial model framework as a trained image classification model after updating the parameters.

3. The medical image classification method of claim 2, wherein inputting the classification prediction values into the CE loss function and the ACE loss function, and obtaining a loss value comprises:

inputting the classification prediction values corresponding to medical image samples labeled as one type into the CE loss function, and obtaining a loss value of the CE loss function;

inputting the classification prediction values corresponding to medical image samples with generic label into the ACE loss function, and obtaining a loss value of the ACE loss function.

4. The medical image classification method of claim 2, wherein the medical image is a computed tomography (CT) image, classifying the medical image by using the image classification model, and obtaining a classification result of the medical image comprises:

classifying the CT image by using the image classification model, and obtaining a classification result of the CT image, the CT image comprising: non-contrast phase or arterial phase or venous phase or delay phase.

5. The medical image classification method of claim 3, further comprising:

calculating a probability of a different classification of the medical image samples by using a normalized exponential function;

constructing a classification probability relationship according to the calculated probability;

constructing the ACE loss function according to the classification probability relationship and the CE loss function.

6. The medical image classification method of claim 5, wherein the medical image is a computed tomography (CT) image, classifying the medical image by using the image classification model, and obtaining a classification result of the medical image comprises:

classifying the CT image by using the image classification model, and obtaining a classification result of the CT image, the CT image comprising: non-contrast phase or arterial phase or venous phase or delay phase.

7. The medical image classification method of claim 6, wherein the classification probability relationship is expressed as:

$$PC = PA + PV + PD = \frac{\exp(WA) + \exp(WV) + \exp(WD)}{\Sigma_i \exp(wi)},$$

wherein the PC is a total probability of a phase prediction value of the arterial, of the venous, and of the delay phase, the PA is a probability of a phase prediction value of the arterial phase, the PV is a probability of a phase prediction value of the venous phase, and the PD is a probability of a phase prediction value of delay phase, exp( . . . ) is an exponential function, w( . . . ) is a logarithmic function, and i is a positive integer; and the ACE loss function is expressed as:

$$L_{ACE} = -\log(PC) = -\log\left(\frac{\exp(WA) + \exp(WV) + \exp(WD)}{\Sigma_i \exp(wi)}\right),$$

wherein log( . . . ) is a logarithmic function.

8. The medical image classification method of claim 1, wherein the medical image is a computed tomography (CT) image, classifying the medical image by using the image classification model, and obtaining a classification result of the medical image comprises:

classifying the CT image by using the image classification model, and obtaining a classification result of the CT image, the CT image comprising: non-contrast phase or arterial phase or venous phase or delay phase.

9. An electronic device, comprising:

a processor; and a memory storing a plurality of instructions, which when executed by the processor, causes the processor to:

receive a medical image;

input the medical image into an image classification model, which provides a cross entropy (CE) loss function and an aggregated cross entropy (ACE) loss function, wherein according to the ACE loss function, image samples with generic label are used as input data during model training, wherein the image classification model comprises a plurality of three dimensional (3D) convolution layers, a squeeze and excitation (SE) layer and a plurality of fully connected layers;

classify the medical image by using the image classification model and obtain a classification result of the medical image.

10. The electronic device of claim 9, before receive the medical image, the processor further:

obtains a plurality of medical image samples, the medical image samples comprising: medical image samples labeled as one type, medical image samples with generic label, and unlabeled medical image samples;

re-samples the plurality of medical image samples, and obtains preprocessed image samples with a uniform format;

extracts partial image features from the preprocessed image samples using a plurality of three dimensional (3D) convolution layers in an initial model framework;

performs a global pooling operation on the partial image features using a Squeeze and Excitation (SE) layer in the initial model framework, and obtains a multiplicative factor of each feature channel, and obtains global image features by weighting the multiplicative factor into the partial image features;

integrates the global image features by using a plurality of fully connected layers in the initial model framework, and obtains classification prediction values;

inputs the classification prediction values into the CE loss function and the ACE loss function, and obtains a loss value;

updates parameters of the initial model framework according to the loss value by using a back propagation algorithm;

when the loss value of the CE loss function and the loss value of the ACE loss function are in a convergence state, determines the initial model framework as a trained image classification model after updating the parameters.

11. The electronic device of claim 10, the processor further:

inputs the classification prediction values corresponding to medical image samples labeled as one type into the CE loss function, obtaining a loss value of the CE loss function;

inputs the classification prediction values corresponding to medical image samples with generic label into the ACE loss function, obtaining a loss value of the ACE loss function.

12. The electronic device of claim 11, the processor further:

calculates a probability of different classification of the medical image samples by using a normalized exponential function;

constructs a classification probability relationship according to the calculated probability;

constructs the ACE loss function according to the classification probability relationship and the CE loss function.

13. The electronic device of claim 12, wherein the medical image is a computed tomography (CT) image, the processor further:

classifies the CT image by using the image classification model, and obtains a classification result of the CT image, the CT image comprises: non-contrast phase or arterial phase or venous phase or delay phase.

14. The electronic device of claim 13, wherein the classification probability relationship is expressed as:

$$PC = PA + PV + PD = \frac{\exp(WA) + \exp(WV) + \exp(WD)}{\Sigma_i \exp(wi)}$$

wherein the PC is a total probability of a phase prediction value of the arterial, of the venous, and of the delay phase, the PA is a probability of a phase prediction value of arterial phase, the PV is a probability of a phase prediction value of venous phase, the PD is a probability of a phase prediction value of delay phase, exp( . . . ) is an exponential function, w( . . . ) is a logarithmic function, and i is a positive integer; and the ACE loss function is expressed as:

$$L_{ACE} = -\log(PC) = -\log\left(\frac{\exp(WA) + \exp(WV) + \exp(WD)}{\Sigma_i \exp(wi)}\right)$$

wherein log( . . . ) is a logarithmic function.

15. The electronic device of claim 10, wherein the medical image is a computed tomography (CT) image, the processor further:

classifies the CT image by using the image classification model, and obtains a classification result of the CT image, the CT image comprises: non-contrast phase or arterial phase or venous phase or delay phase.

16. The electronic device of claim 9, wherein the medical image is a computed tomography (CT) image, the processor further:

classifies the CT image by using the image classification model, and obtains a classification result of the CT image, the CT image comprises: non-contrast phase or arterial phase or venous phase or delay phase.

* * * * *